United States Patent [19]
Walsh et al.

[11] Patent Number: 6,126,728
[45] Date of Patent: Oct. 3, 2000

[54] OVEN AIR FLOW DIRECTOR

[75] Inventors: George P. Walsh, Wilmington, Del.;
Roger A. Brown, Philadephia, Pa.;
William H. Wilson, Newark, Del.

[73] Assignee: Agilent Technologies, Inc., Santa Clara, Calif.

[21] Appl. No.: 09/183,171

[22] Filed: Oct. 30, 1998

[51] Int. Cl.$^7$ ............................................... B01D 15/08
[52] U.S. Cl. .................................... 96/101; 95/87
[58] Field of Search .................... 95/82, 87; 96/101–107

[56] References Cited

U.S. PATENT DOCUMENTS

| | | | |
|---|---|---|---|
| 3,165,147 | 1/1965 | Roof et al. | 96/102 X |
| 3,305,000 | 2/1967 | Bullen et al. | 96/102 X |
| 4,038,055 | 7/1977 | Varano et al. | 96/102 |
| 4,599,169 | 7/1986 | Ray | 96/101 X |
| 4,771,628 | 9/1988 | Sisti et al. | 96/101 X |
| 4,869,876 | 9/1989 | Arfman et al. | 96/102 X |
| 5,552,042 | 9/1996 | LeFebre et al. | 96/101 X |
| 5,634,961 | 6/1997 | Gordon | 95/17 |
| 5,744,029 | 4/1998 | Li et al. | 96/101 X |
| 5,807,426 | 9/1998 | Ohtsuki et al. | 96/102 |
| 5,830,262 | 11/1998 | Marchini et al. | 96/105 |

FOREIGN PATENT DOCUMENTS

| | | | |
|---|---|---|---|
| 2400389 | 7/1975 | Germany | 96/101 |
| 60-027855 | 2/1985 | Japan | 96/101 |
| WO82/01662 | 5/1982 | WIPO | 96/101 |

*Primary Examiner*—Robert H. Spitzer

[57] ABSTRACT

An airflow director constructed for use with a separation column in a temperature-controlled air bath in a chromatographic oven cavity, wherein the airflow director includes at least a first baffle locatable with respect to the separation column and to the low pressure and high-pressure regions of the air bath, wherein the baffle is configured to direct air flow away from the high-pressure region before passing over the separation column. The temperature-controlled air thereby mixes with oven cavity air before passing over the separation column, which is thereby less subject to thermal gradients.

5 Claims, 5 Drawing Sheets

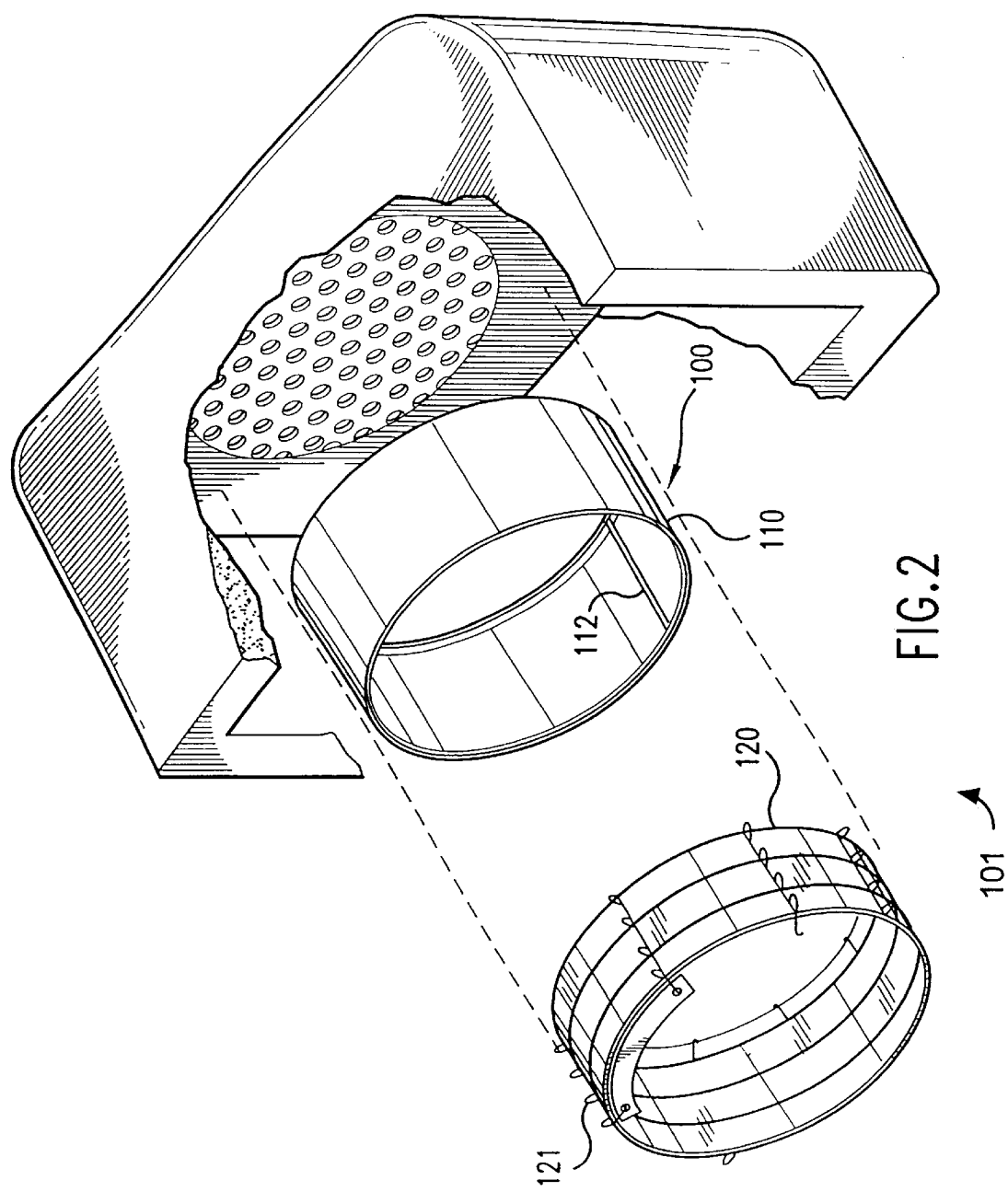

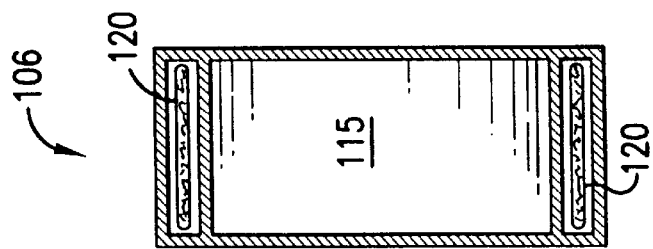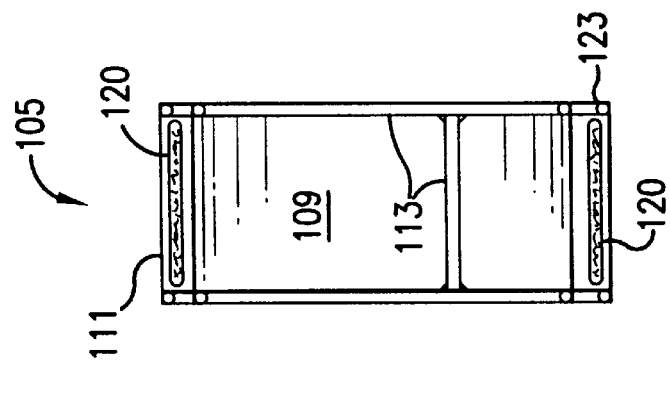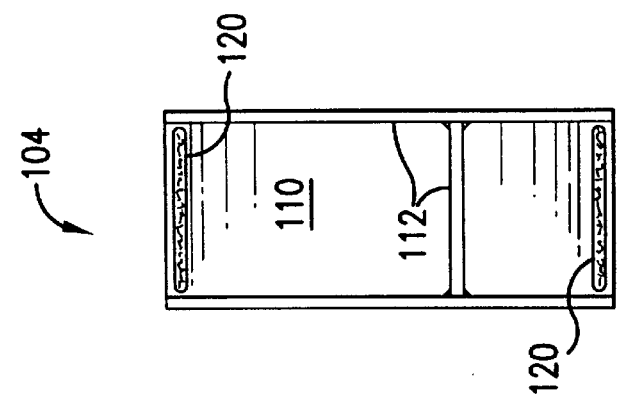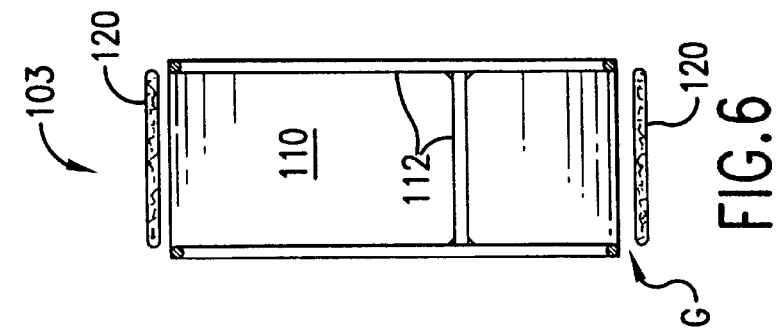

OVEN AIR FLOW DIRECTOR

FIELD OF THE INVENTION

The present invention relates to apparatus for improved operation of a separation column in an analytical apparatus, and more particularly with an oven airflow director for use in an oven in a chromatographic instrument.

BACKGROUND OF THE INVENTION

The basic components of a chromatographic instrument (hereinafter, chromatograph) include an injection port for introducing a sample to be examined into a stream of carrier medium, a separation column attached to the injection port, and a temperature-controlled zone in which the column is mounted. Typically, the column is constructed in the form of a helix of tubing containing a stationary phase that causes some of the constituents of the sample to elute at different times. The output end of the separation column is attached to a detector for producing a signal indicative of the concentration of the constituents being eluted.

With reference to FIG. 1, a portion of a typical chromatograph is illustrated, wherein the temperature-controlled zone is contained within an oven 10. The oven 10 typically comprises a thermally insulated oven housing 20 having an opening for access to the oven interior 18. An oven heater includes a controlled heating element and a motor-driven stirring fan (not shown) situated behind a perforated section 21 in a shroud 22. The injection port and detector (not shown) are attached to respective pneumatic fittings 12, 14 on the oven 10. The separation column 16 is typically provided in the form of a coil of tubing mounted on a basket 17 positioned within the oven interior 18 such that the inlet and outlet ends of the separation column 16 may be attached to the pneumatic fittings 12, 14.

In analyzing most samples, the heating element is controlled so as to vary the temperature of the oven according to a predetermined temperature profile. It is also known to operate the stirring fan to draw oven cavity air into the heater through the perforated section 21 and force heated air from the oven heater through the periphery of the shroud 22 and into the oven cavity.

The stirring fan mixes the heated air from the heating element with oven cavity air, with the goal of creating a uniform thermal profile. The stirring fan is thus employed in an attempt to circulate an air "bath" throughout the oven cavity so as to minimize thermal gradients that could adversely affect the performance of the chemical process occurring within the column. Conventional stirring fans typically employ a mixed flow impeller to create a vortex airflow. The resulting air bath develops a high pressure region of newly heated air at the periphery of the shroud and a low pressure region in the center of the oven interior. This technique is intended to maximize the time for air mixing and to employ the oven walls as a thermal damper to minimize thermal gradients.

SUMMARY OF THE INVENTION

We have determined that as the volume of the oven is reduced, the heated air from the conventional heater has insufficient time to mix with the oven air. Furthermore, we have found that the heated air from the heater assembly is not well isolated from the column as it flows from the periphery of the shroud. In fact, we have observed that an oven of conventional design, if reduced in volume, will exhibit a "short circuit" path between the high-pressure and low pressure regions of the conventional oven heater described hereinabove. That is, a noticeable portion of the heated air generated from a conventional oven heater and shroud assembly has been observed to be drawn across a portion of the separation column and into the low pressure region at the oven heater intake (e.g., the perforated section 21 of FIG. 1) without experiencing any substantial traverse of the oven cavity and without being subject to the desired mixing with oven air.

Accordingly, a separation column, generally provided in the form of a helix of sufficient diameter to permit it to be oriented so that desirable air flow passes through the center of the helix, has been observed to be subject to undesirable temperature gradients caused by the pre-disposition of the newly heated air to move immediately from the high-pressure region to the low pressure region.

Accordingly, an airflow director may be constructed according to the present invention to include at least a first baffle locatable with respect to a column and the high-pressure region and the low pressure region in a temperature-controlled air bath system, wherein the baffle prevents the premature transit of temperature-controlled air flow directly from the high-pressure region (e.g., the periphery of a conventional oven heater shroud) to the low pressure region (e.g., the perforated section). Instead, the temperature-controlled air exiting the high-pressure region is directed to a portion of the oven cavity substantially away from the high-pressure region, allowing it an improved opportunity to mix with oven cavity air and optionally to encounter a thermal mass of the oven, before such temperature-controlled air has the opportunity to return to the low pressure region. In doing so, the air bath passing over the separation column is less likely to induce thermal gradients in the separation column.

The contemplated airflow director also produces a secondary effect wherein the air movement in the immediate vicinity of the column is much slower than the air movement in the remainder of the air bath. Furthermore, the baffle serves as a low-mass thermal damper to further aid in reducing thermal gradients. The baffle also serves to block the direct transmission of radiant heat (e.g., infrared energy) that may be emitted by some heating systems, such as a resistive wire heater.

As a result, a separation column operated with the contemplated airflow director experiences a more uniform temperature profile, thus yielding smoother and more symmetrical peak shaping.

In another aspect of the invention, the airflow director may be used to position the column in the oven interior in a predetermined, repeatable fashion. In certain configurations of the airflow director, unwrapped column segments may be advantageously retained on the baffle by rotating the column basket on the baffle until such "service loops" are taken up.

A first preferred embodiment of the airflow director includes a baffle that is sized and configured to receive a separation column mounted thereon, and wherein the baffle is located with respect to the oven heater so as to substantially extend the air bath circuit from the high-pressure region to the low pressure region.

In another preferred embodiment, the airflow director includes first and second baffles concentrically mounted about a coiled separation column, wherein the first baffle is located radially inward of the coiled separation column and the second baffle is located radially outward of the coiled separation column, such that the coiled separation column is interposed between the first and second baffles.

In another preferred embodiment, the airflow director includes a substantially continuous baffle envelope mounted about a coiled separation column, wherein the envelope substantially encloses the coiled separation column, such that the coiled portion of the separation column is enclosed within the continuous baffle envelope.

In another preferred embodiment, the airflow director includes a baffle having support means for supporting the baffle in the oven interior.

In another preferred embodiment, the airflow director includes a baffle integrated in the oven cavity enclosure as an extension in a wall of the oven cavity enclosure.

BRIEF DESCRIPTION OF THE DRAWINGS

The present invention will be better understood, and its numerous objects and advantages will become apparent by reference to the following detailed description of the invention when taken in conjunction with the following drawings, in which:

FIG. 2 is a side perspective, exploded view of a first preferred embodiment of an oven air flow director and an associated separation column constructed according to the present invention.

FIG. 6 is another side sectional view of the oven air flow director of FIG. 5, illustrating the separation column installed on the exterior of the oven air flow director.

FIGS. 7–9 are side sectional views of respective second, third, and fourth embodiments of the oven air flow director of FIG. 2.

DETAILED DESCRIPTION OF THE PREFERRED EMBODIMENTS

Figure 1:
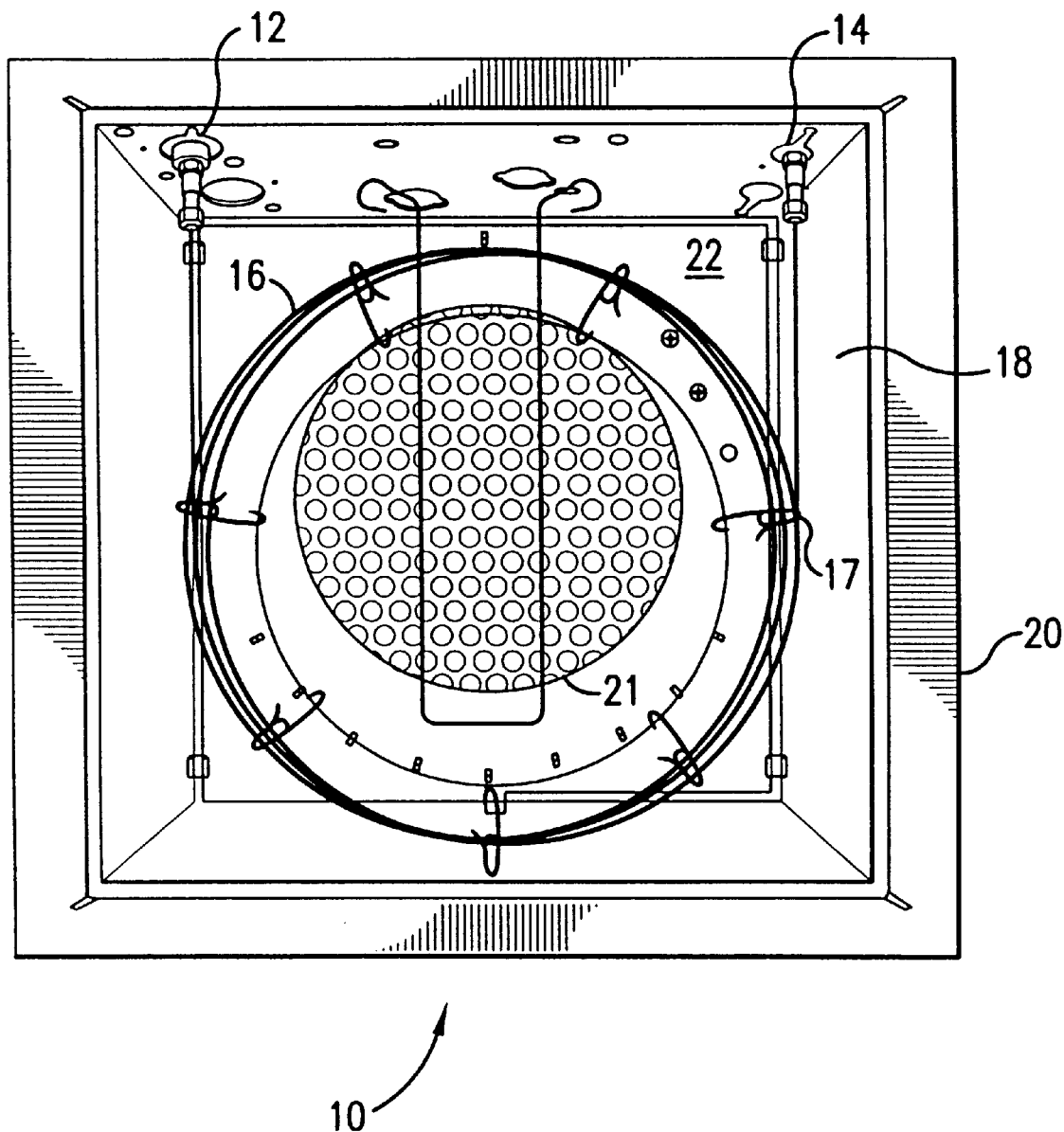
FIG. 1 is a front perspective view of an oven interior in a gas chromatograph constructed in accordance with the prior art.

FIG. 2 is a side perspective, exploded view of a first preferred embodiment 101 of an oven air flow director (hereinafter, director 100) and an associated separation column 120 constructed according to the present invention. In the first preferred embodiment 101, the director 100 is formed of a baffle 110 of thin metal foil attached to a wire frame 112 having suitable dimensions such that the baffle 110 may be fitted to separation column 120 mounted on a column basket 121, such that the column basket 121 is mounted on or within the baffle 110.

As illustrated in FIGS. 3–9, those skilled in the art will appreciate that alternate configurations and dimensions of the baffle 110 may be provided according to the particular dimensions and configuration of the column basket, oven cavity, and so on.

Figure 5:
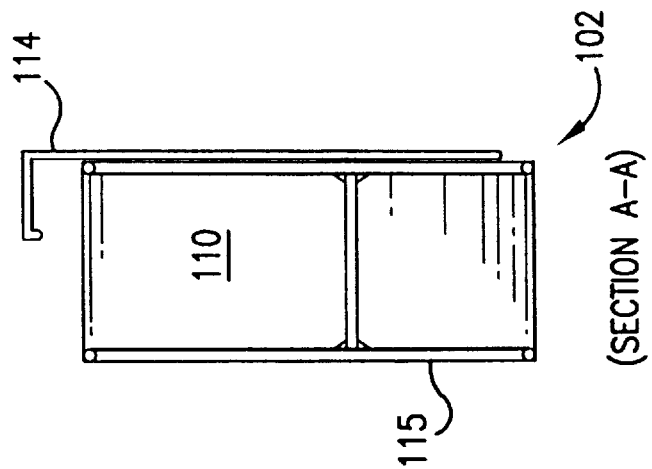
FIG. 5 is of the oven air flow director of FIG. 2.
Figure 4:
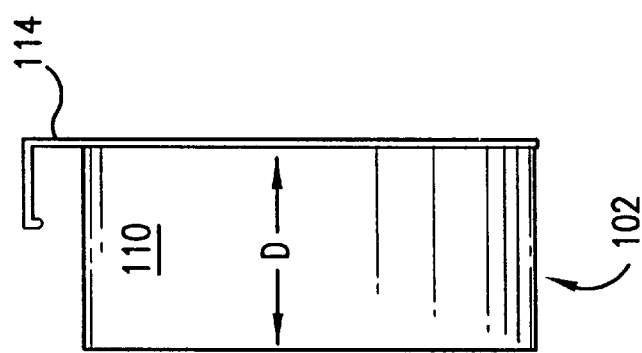
FIG. 4 is of the oven air flow director of FIG. 2.
Figure 3:
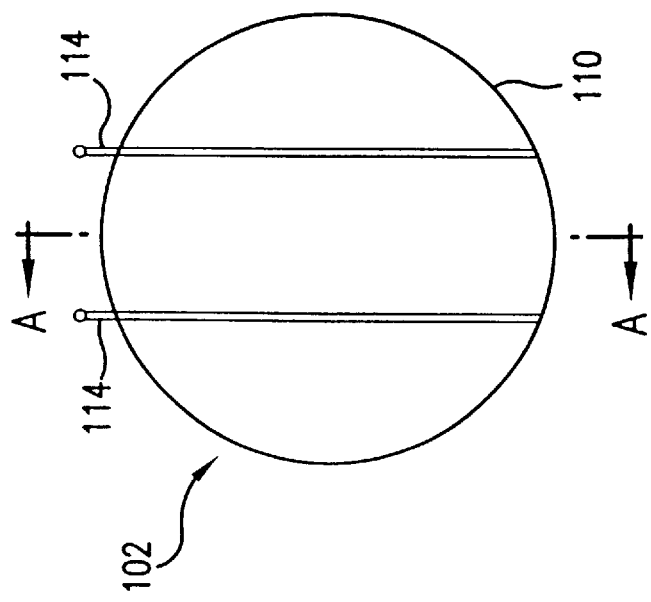
FIG. 3 is an oven air flow director.

As illustrated in FIGS. 3–5, a second preferred embodiment 102 of the director 100 may optionally include means for supporting the baffle 110, such as is supports 114 suitable for attaching the director 100 to an appropriate hanger retention means in an oven interior.

FIG. 6 is side sectional view of a third preferred embodiment 103 of the oven flow director 100, now showing the separation column 120 installed on the exterior of the baffle 110.

FIG. 7 is a side sectional view of a fourth preferred embodiment 104 of the oven flow director 100, wherein the baffle 110 is now sized and configured to fit on the exterior of the separation column 120.

FIG. 8 is a side sectional view of a fifth embodiment 105 of the oven flow director 100 wherein a first baffle 109, mounted on the respective first wire frame 113, is situated within the separation column 120 and a second, larger-diameter baffle 111, mounted on a respective second, larger-diameter wire frame 123, is situated on the exterior of the separation column 120. As a result, the separation column 120 and column basket 121 is interposed, or "sandwiched", between the first and second baffles 109, 111.

Figure 10:
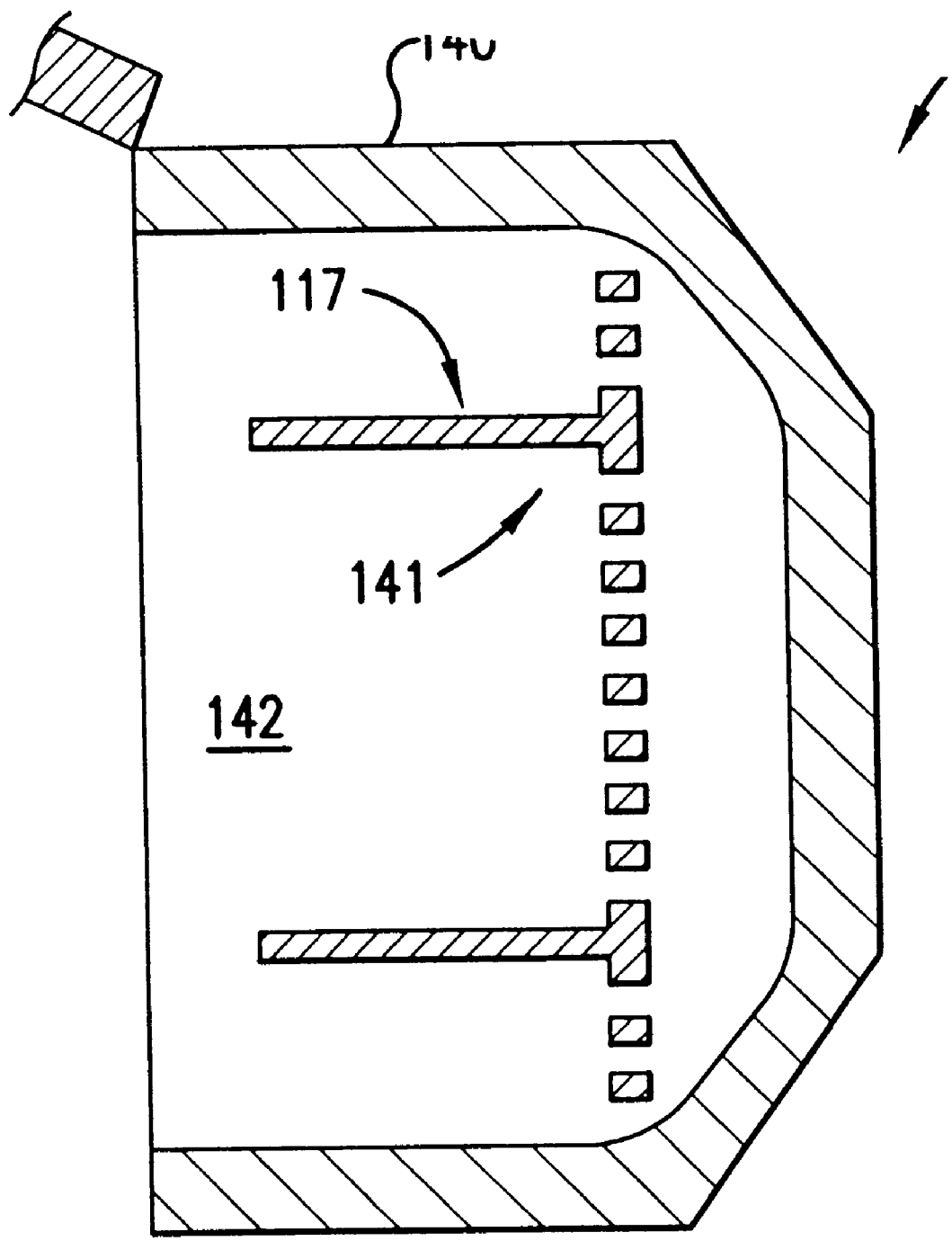
FIG. 10 is a top sectional view of a fifth embodiment of the oven air flow director of FIG. 2.

FIG. 9 is a side sectional view of a sixth embodiment 106 of the oven flow director 100 wherein the separation column 120 and column basket 121 is enclosed within a baffle envelope 115. FIG. 10 is a side sectional view of a seventh embodiment 107 of the oven flow director 100 wherein at least one of the interior walls 140 that define the interior of the oven cavity 142, such as the shroud 141, includes an integral baffle 117 extending therefrom.

Experimental results have indicated that the contemplated airflow director 100 may benefit from one or more structural adaptations of the illustrated embodiments. Some experimental results indicate that the depth D of baffle 110 should be made sufficiently deep to support the entire width of a basket. In other implementations, the depth D of the baffle 110 may be undersized such that the coils of the separation column 120 exhibit some overhang beyond the edges of the baffle 110. In still other implementations, a selectable gap G between the basket 121 and the baffle 110 may be established to allow greater airflow between the baffle 110 and the basket 121.

Experimental results have also indicated that for some implementations, a single baffle 110 that is sized to fit snugly within the basket 121 offers useful improvement in peak shapes; whereas, in other implementations, improvements in peak shape were observed when a substantial gap (on the order of approximately 5 millimeters) was provided between a single baffle 110 and the basket 121.

Still other experimental results have indicated that the airflow director may be advantageously configured as shown in FIG. 9, wherein the airflow director is configured as a baffle envelope 115 constructed to enclose the majority of the separation column, thus allowing the inlet and outlet ends of the separation column 120 to be exposed for appropriate connections to ancillary devices.

Whereas the preferred embodiments of the director described herein are illustrated as being generally cylindrical, it is contemplated that additional embodiments may be provided in certain configurations so as to reduce thermal gradients in separation columns in an oven, wherein either or both of the separation column and the oven has a shape or configuration other than those shown herein. For example, the preferred embodiments described herein may be configured to conform to a separation column, basket, or oven cavity having an oblate, oval, rectangular, circular, etc. configuration, which would necessitate some adaptation of the illustrated embodiments of the oven director 100. However, all of such adaptations are believed to be within the spirit and scope of the present invention. Preferred embodiments of the airflow director may be formed of any material having sufficient structural rigidity for accomplishing the desired airflow direction described herein, and having sufficiently low thermal mass and high thermal conductivity, so as to avoid significant thermal gradients in, for example, the baffle itself. Experimental versions of the baffle 110 have been constructed from 0.002 inch to 0.003 inch stainless-steel foil or aluminum foil. Suitable alternative materials include nickel foil and drawn metal cylinder material. The airflow director 100 may also be formed of materials susceptible to electroforming, such as nickel.

What is claimed is:

1. An airflow director for use with a separation column provided in the form of a coil in a temperature-controlled air bath provided in a chromatographic oven cavity, comprising:

a baffle comprising a cylinder configured for mounting the coiled separation column thereon with the baffle located radially inward of the separation column and located with respect to a low pressure region and a high-pressure region of the air bath, wherein the baffle is configured to prevent the direct transition of air flow from the high pressure region to the low pressure region, whereby temperature-controlled air in the air bath is directed away from the high-pressure region before passing over the separation column.

2. An airflow director for use with a separation column provided in the form of a coil in a temperature-controlled air bath provided in a chromatographic oven cavity, comprising:

a baffle comprising a cylinder configured for mounting the coiled separation column thereon with the baffle located radially outward of the separation column and located with respect to a low pressure region and a high-pressure region of the air bath, wherein the baffle is configured to prevent the direct transition of air flow from the high pressure region to the low pressure region, whereby temperature-controlled air in the air bath is directed away from the high-pressure region before passing over the separation column.

3. An airflow director for use with a separation column provided in the form of a coil in a temperature-controlled air bath provided in a chromatographic oven cavity, comprising:

first and second cylindrical baffles concentrically mounted about the coiled separation column, the first baffle being located radially inward of the coiled separation column and the second baffle being located radially outward of the coiled separation column, a major portion of the coiled separation column being interposed between the first and second baffles, and located with respect to a low pressure region and a high-pressure region of the air bath, wherein the baffle is configured to prevent the direct transition of air flow from the high pressure region to the low pressure region, whereby temperature-controlled air in the air bath is directed away from the high-pressure region before passing over the separation column.

4. An airflow director for use with a separation column provided in the form of a coil in a temperature-controlled air bath provided in a chromatographic oven cavity, comprising:

a substantially continuous baffle envelope mounted about a coiled separation column, wherein a major portion of the separation column is enclosed within the continuous baffle envelope, and located with respect to a low pressure region and a high-pressure region of the air bath, wherein the baffle is configured to prevent the direct transition of air flow from the high pressure region to the low pressure region, whereby temperature-controlled air in the air bath is directed away from the high-pressure region before passing over the separation column.

5. An airflow director for use with a separation column in a temperature controlled air bath provided in a chromatographic oven cavity, comprising:

the oven cavity defined by an enclosure having at least one wall;

a baffle comprising a baffle integrated in the enclosure as an extension in the wall of the enclosure of the oven cavity and locatable with respect to the separation column and to a low pressure region and a high-pressure region of the air bath, wherein the baffle is configured to prevent the direct transition of air flow from the high pressure region to the low pressure region, whereby temperature-controlled air in the air bath is directed away from the high-pressure region before passing over the separation column.

* * * * *